(12) United States Patent  (10) Patent No.: US 7,351,193 B2
Forman et al.  (45) Date of Patent: Apr. 1, 2008

(54) TREATMENT OF AGE-RELATED MACULAR DEGENERATION

(75) Inventors: Michael Forman, Los Gatos, CA (US); Paul A. Lovoi, Saratoga, CA (US); Peter C. Smith, Half Moon Bay, CA (US)

(73) Assignee: Xoft, Inc., Fremont, CA (US)

( * ) Notice: Subject to any disclaimer, the term of this patent is extended or adjusted under 35 U.S.C. 154(b) by 0 days.

(21) Appl. No.: 11/234,824

(22) Filed: Sep. 22, 2005

(65) Prior Publication Data

US 2006/0078087 A1  Apr. 13, 2006

Related U.S. Application Data

(63) Continuation-in-part of application No. 10/635,421, filed on Aug. 6, 2003, now abandoned.

(51) Int. Cl.
*A61N 5/00* (2006.01)

(52) U.S. Cl. .......................................................... 600/3

(58) Field of Classification Search ................ 600/1–8, 600/452, 459; 128/897–899; 378/65, 119
See application file for complete search history.

(56) References Cited

U.S. PATENT DOCUMENTS 5,637,073 A * 6/1997 Freire ............................ 600/3

| 6,443,881 | B1 * | 9/2002 | Finger ........................... 600/1 |
| 2002/0131699 | A1 * | 9/2002 | Raguin et al. ................. 385/33 |
| 2003/0179854 | A1 * | 9/2003 | Jaafar ........................... 378/119 |
| 2005/0027156 | A1 * | 2/2005 | Pulido et al. ................... 600/1 |

* cited by examiner

*Primary Examiner*—John P Lacyk
(74) *Attorney, Agent, or Firm*—Thomas M. Freiburger

(57) ABSTRACT

Age-related macular degeneration is treated by radiation delivered from a miniature x-ray tube inserted via a catheter around the globe of the eye, to a position behind the macula. The process can employ an applicator with several parallel guides, inserted around the eye to receive the catheter with x-ray tube (or an isotope) at a matrix of different positions. Methods are described for properly locating the catheter and x-ray tube, using illumination on the catheter and viewing through the front of the eye, or sensors on the catheter and a scanned beam shone from the front of the eye. Fluorescent material excited by x-rays can also be used. Also described are methods and devices for immobilizing the probe once properly located in the eye, for standoff of the x-ray tube from the target tissue, and for achieving prescription radiation dose in the choroid while eliminating dose to adjacent tissues. The x-ray treatment can be enhanced using a radiosensitizing drug, and can be combined with PDT.

46 Claims, 11 Drawing Sheets

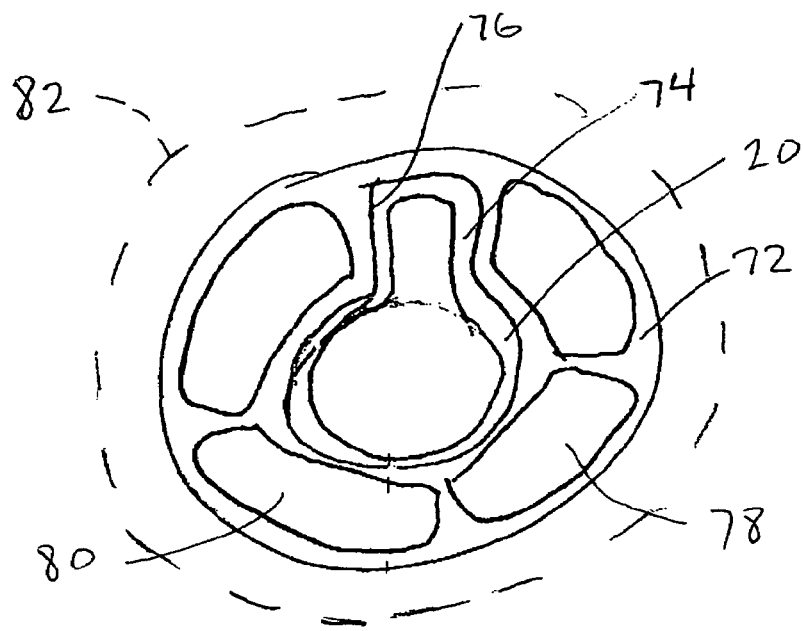
FIG. 11
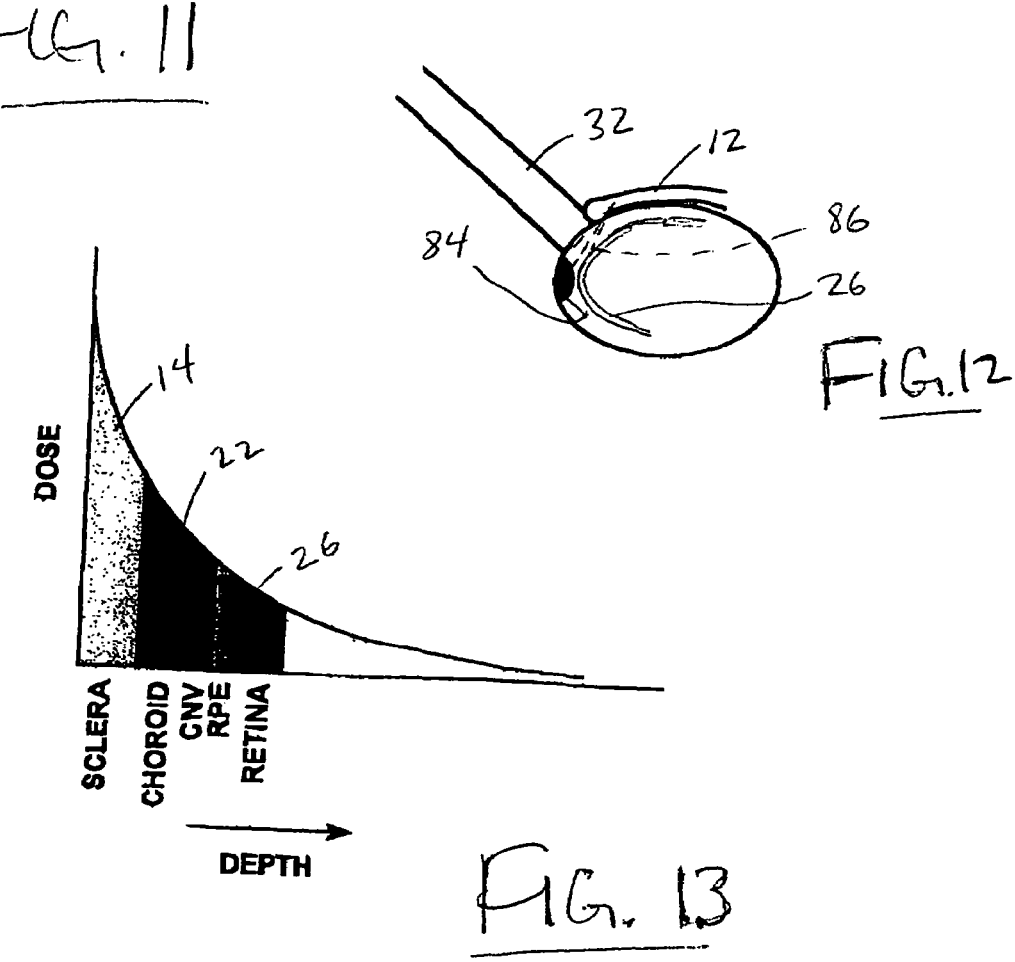
FIG. 12
FIG. 13

TREATMENT OF AGE-RELATED MACULAR DEGENERATION

This application is a continuation-in-part of application Ser. No. 10/635,421, filed Aug. 6, 2003 now abandoned.

BACKGROUND OF THE INVENTION

This invention concerns treatment of wet age-related macular degeneration (AMD) in the eye, and in particular concerns use of radiation to treat such macular degeneration, the radiation being administered from behind the sclera. Treatment of ocular tumors also forms a part of the invention.

Wet age-related macular degeneration has been the leading cause of blindness in the United States, and a leading cause in the world. It is characterized by the growth of abnormal blood vessels from the choroidal membrane at the back of the eye, in the macular area of the retina including the fovea and immediately surrounding regions. This is called "choroidal neovascularization" (CNV). The term "wet" refers to the fact that these abnormal blood vessels leak and damage the macula, causing central vision distortion. Thus, the highest resolution vision of the patient is severely compromised or lost.

Approximately ten percent of AMD cases comprise wet AMD, and this is the type which can lead to blindness. Dry AMD comprises approximately ninety percent of AMD cases, but a certain percentage of these (approximately ten percent) eventually progress to wet AMD.

Of wet AMD patients, approximately seventy percent of these cases are classic wet AMD, while approximately thirty percent are what is known as occult AMD. In both cases CNV occurs, invading the choroid and the space above the choroid with proliferating blood vessels which cause damage. In the case of classic AMD, the new blood vessels remain essentially intact, while in occult AMD the blood vessels leak, form a somewhat amorphous mass, and obscure the ability of a physician to see the vessel through an ophthalmoscope. Thus, any treatment aimed specifically at these vessels, requiring visual identification and location of the vessels, fails for occult AMD.

There have been several approaches to treatment of wet AMD. In both photodynamic therapy (PDT) and transpupillary thermal therapy (TTT) laser beams are used, directed through the front of the eye. These have had varying degrees of effectiveness, with PDT generally being the more effective of the two. In PDT, the treatment consists of a administering photosensitizing dye followed by laser treatment, which sensitizes the dye to affect the CNV condition. Results of both TTT and PDT have been less than ideal. With PDT, based on one study, only 15% of AMD patients would meet the Macular Photocoagulation Study Group (MPSG) guidelines for treatment; thus, most AMD patients would not benefit from this treatment. In addition, the cost for this treatment has been extremely high and its cost effectiveness is in question.

It is also noted that although the FDA recommends PDT treatment of patients with predominantly classic choroidal neovascular lesions from AMD, in most cases neovascularization recurred within three months. Thus, patients will probably need three to four treatments per year for this therapy to be effective, and the treatment basically preserves vision rather than improves visual acuity.

Researchers have discovered that x-ray radiation can be effective in treating CNV. Radiation has been administered from external sources, through the temple area, and also via brachytherapy using "plaques" which support radioisotope pellets, these plaques being implanted onto the back side of the eye, against the sclera, by insertion around the exterior of the sclera. These implanted plaques have been left in position for a prescribed duration of time, e.g. about 30 hours, or a range of about 18 to 65 hours, the time necessary to derive a radiation dose of about 17 Gy. Results of one study showed stabilization or sight improvement in about 45% of treated patients. After a seven year follow up, no sight-limiting radiation complications were noted in any patients. Thus, x-ray radiation, particularly administered by brachytherapy, is known to have some efficacy in the stabilization and improvement of the CNV condition of macular degeneration.

U.S. Pat. No. 6,443,881, issued to Paul Finger, describes use of these plaques and methods for locating the plaques using light sources mounted on the plaques.

External beam treatment is difficult and generally limited to highly specialized practitioners, with capital cost for equipment very high. This treatment is difficult for several reasons, including inability to produce a very small beam specific to the target, location of the beam precisely on the target, radiation damage to other structures, including brain tissue, and avoidance of irradiating the optic nerve and retna.

In addition to other limitations discussed above, the use of isotopes is not ideal. They are extremely limited as to choices of specific activity of the isotopes, as well as energy. Further, the isotopes must be shielded during emplacement for brachytherapy, as well as shielded directionally to protect adjacent structures, since the isotopes are isotropic emitters.

A much improved treatment for CNV of macular degeneration would be a controllable x-ray source which can be placed minimally adjacent to the macula, with accurate placement, with reliably accurate directional emission, and which can be controlled as to depth of radiation penetration as well as dose. These are objects of the present invention described below.

SUMMARY OF THE INVENTION

This invention is a method and device by which a miniature x-ray source is inserted around the globe of the eye, minimally invasively, to locate the source directly adjacent to the macula, behind the eye and against the sclera. Only the thin membrane, the conjunctiva, that forms the interface between the eye socket and the globe of the eye from the outside world is slit to allow insertion of the source or a guide. The miniature x-ray tube is switchable off/on as well as controllable, in preferred embodiments, as to voltage (penetration) and current (dose). Insertion of the source is via a catheter/probe which is inserted around the globe to the back of the eye and positioned adjacent to the target tissue. The miniature x-ray tube within the catheter may be on the order of about 1 mm in diameter with a length of approximately 7 mm (although dimensions can vary and the eye could accept larger dimensions). By this device, a therapeutic dose of ionizing radiation is delivered to the abnormal vessels in the choroid layer. This therapeutic radiation tends to seal or close the bleeding vessels through a process that causes vessel fibrosis. Adjacent tissue cells which are not actively proliferating are less affected by the radiation, as is well known.

An important advantage of delivering ionizing radiation from the back of the eye is that a therapeutic dose can be given to the lesion without damaging structures of the eye, i.e. the lens, retina and optic nerve. The membranes at the back of the eye are relatively radioresistant.

The invention encompasses a method and means for accurate location of the catheter or probe and x-ray tube behind the eye. Several different guidance techniques can be used. In accordance with one technique a bump or ridge is provided on the probe or on the guide, forming a moving mound on the retina, as the device is manipulated, visible to the physician from the front of the eye. This provides a fiducial for the physician to accurately locate the anode end of the x-ray tube. Another approach is using light or invisible radiation, directed from the front of the eye, as a tool to locate the probe either spatially or temporally. As one example, a light emitting device from the front of the eye can generate a series of expanding rings of light. These can be sensed by a plurality of sensors on the exterior of the probe, the tissues from the retina to the back of the sclera being relatively translucent. Even though the rings of light will be somewhat scattered when reaching these sensors, their peaks can be detected and averaged to give the center of each to reveal sufficient information when fed back to the console to determine which direction the probe should be moved to effectively center the device and align the radiation source to the macula.

Infrared radiation can be used advantageously in location of the probe. IR can be directed in from the front of the eye, invisible to the patient and thus not uncomfortable to the patient, and this radiation will penetrate through the retina, choroid and sclera to the sensors on the device.

Another alignment device can have light sources positioned on the probe itself, as in the Finger patent referenced above. By the invention these light sources can be cleaved optical fibers or polished fibers with redirecting reflectors at the fiber ends (microprisms), with the origin of the light being back in the console. These fiber ends can serve as "headlights" to locate the probe by reference to the position of the light sources as they appear from the front of the eye. Other variations can include color gradations shone through the front of the eye, a grid of light patterns, or other devices involving the sensing of light from either the probe or from the front of the eye. A modified embodiment uses fluorescence of a material struck by the x-rays to enable seeing the location of the x-ray beam by looking into the front of the eye. A fluorescence material could be put into the blood or the ocular fluid to fluoresce with short bursts of x-ray radiation to locate the device. Alternatively, the tube itself can have a fluorescing material, to glow when excited by x-rays and visually locate the probe.

With the invention the radiation dose and depth can be matched to the prescription for the CNV condition, while minimizing radiation to healthy adjacent structures. Several parameters are adjustable to achieve this. In addition, the x-ray tube in the probe preferably is made directional, and an ideal window of radiation can be provided for the treatment as desired, relative to the distance of the treatment area and the width of the treatment area as seen from the x-ray tube.

Filtration of the x-ray beam from the miniature tube can be put in place if needed. This can greatly reduce low-energy emissions (i.e. "hardening" the beam), thus reducing dose in the near field, i.e. the sclera, where radiation is not desired. This in combination with standoff of the source after placement and adjustment of voltage, enables optimizing dose to the choroid, sclera and retina.

It is important that the probe be immobilized during treatment. Several methods can be used. The "bump" on the probe device described above can be inflatable, thus being inserted flattened but inflated (with liquid) when near the macula. Further inflation can help hold the probe against the adjacent tissues (and also stands the source off from the tissue as described below). Another inflatable balloon can be at the back side of the probe, and a further balloon(s) can be located on the probe proximal to the x-ray source for further immobilization of the probe.

In a variation of the probe as described above, the device first inserted around the globe of the eye is a guide device or applicator, wide and flat and with two, three or more parallel channels or guides within which a probe with an x-ray source can be inserted. This allows the treatment to be administered in steps at many different positions, to reduce the dose to the immediately adjacent sclera while maintaining the desired dose to the macula. The on positions of a switchable x-ray source can be stepped in a pattern such as a 3×3 grid, or with continuous pullback. A similar procedure can be carried out with isotopes (if desired the isotope would be shielded except during application and would be continuously pulled back). The applicator or guide device can have one or more immobilizing devices as described above, and it can have any of the various precision loading devices and methods also described above.

Another aspect of the invention is that drugs can be used to enhance the effectiveness of the radiation treatment, thus allowing lower radiation doses to be administered. Similar to the concept of PDT described above, radiation-enhancing drugs can be administered systemically, causing the irradiated regions to be more sensitive to radiation, but having no (or limited) effect on the body tissues in non-irradiated areas.

It is therefore among the objects of the invention to improve radiation therapy as a treatment for wet exudive macular degeneration, by use of a probe having a controllable radiation source which can be accurately located behind the macula for accurate delivery of the radiation. These and other objects, advantages and features of the invention will be understood from the following description of preferred embodiments, considered along with the drawings.

DESCRIPTION OF THE DRAWINGS

FIG. 11 is a schematic sectional view showing "keying" of an x-ray source within a surrounding sheath containing cooling channels.

FIG. 12 is a sectional schematic view showing tangential or chordal radiation with respect to the globe of the eye, from the x-ray source toward the macula.

FIG. 13 is a graph of dose versus depth of penetration of radiation, i.e. a dose profile for one embodiment of the system in method of the invention.

DESCRIPTION OF PREFERRED EMBODIMENTS

Figure 1:
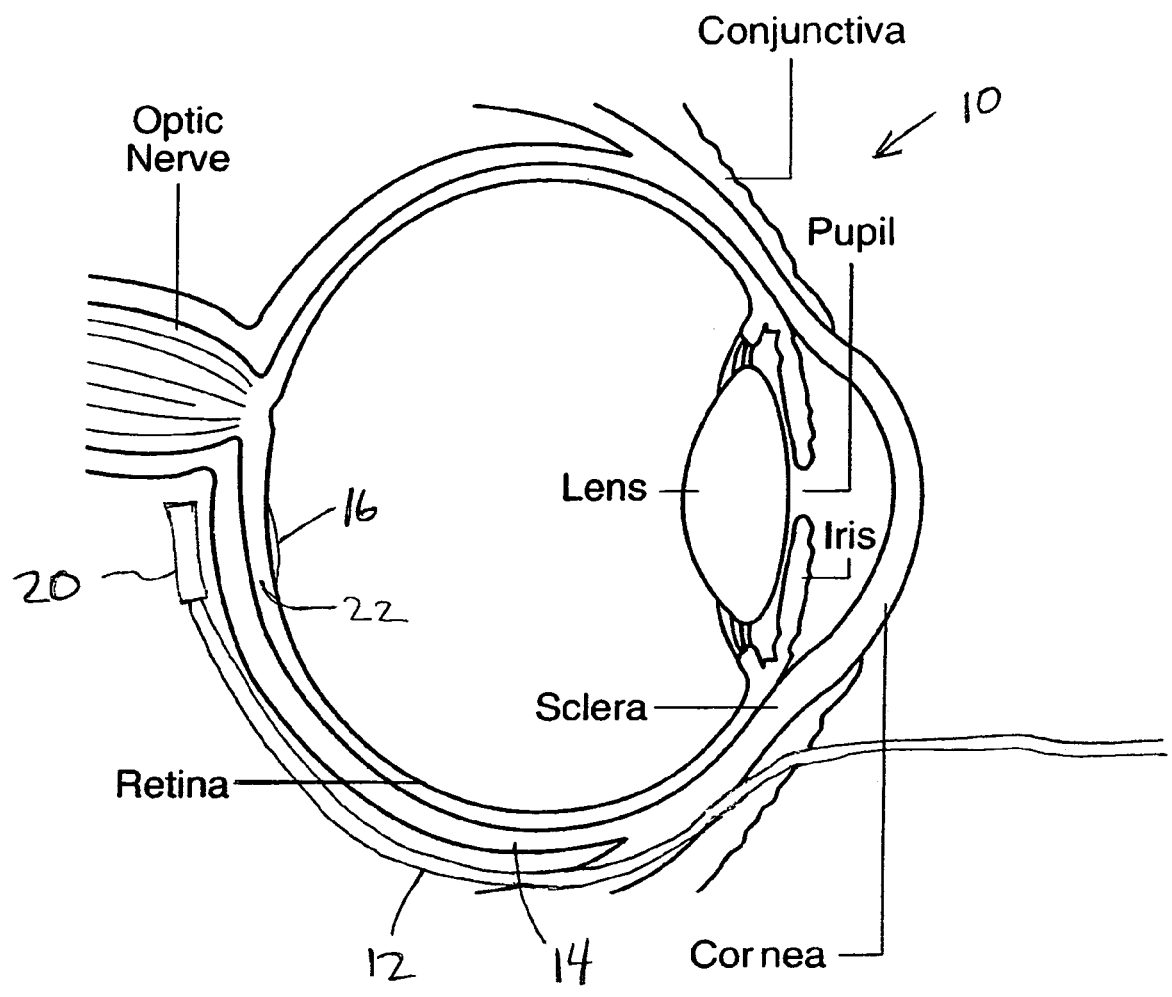
FIG. 1 is a schematic view in sectional plan showing an eye and a catheter being inserted minimally invasively around the globe, behind the macular region.

FIG. 1 of the drawings shows a patient's eye 10, generally in plan view and cross section, and schematically indicates a probe or catheter device 12 inserted around the globe of the eye, along the surface of the sclera 14. The macula, or macular region, a region of the retina of the eye, is shown at 16. The probe or catheter device 12, which is shown schematically, includes a switchable x-ray source 20 at its distal end. An applicator or guide device may be included, to be inserted around the eye and through which the catheter is inserted. The source 20 preferably comprises an x-ray tube which emits radiation when switched on and which optionally can be varied as to current and voltage, emitting a side-looking directional radiation toward the macula 16, through the sclera 14 and the choroidal membrane or layer immediately behind the macula. The source could be an isotope, with controlled shielding if desired. Accurate positioning of the x-ray source 20 is an important aspect of the invention and is discussed below.

Figure 2:
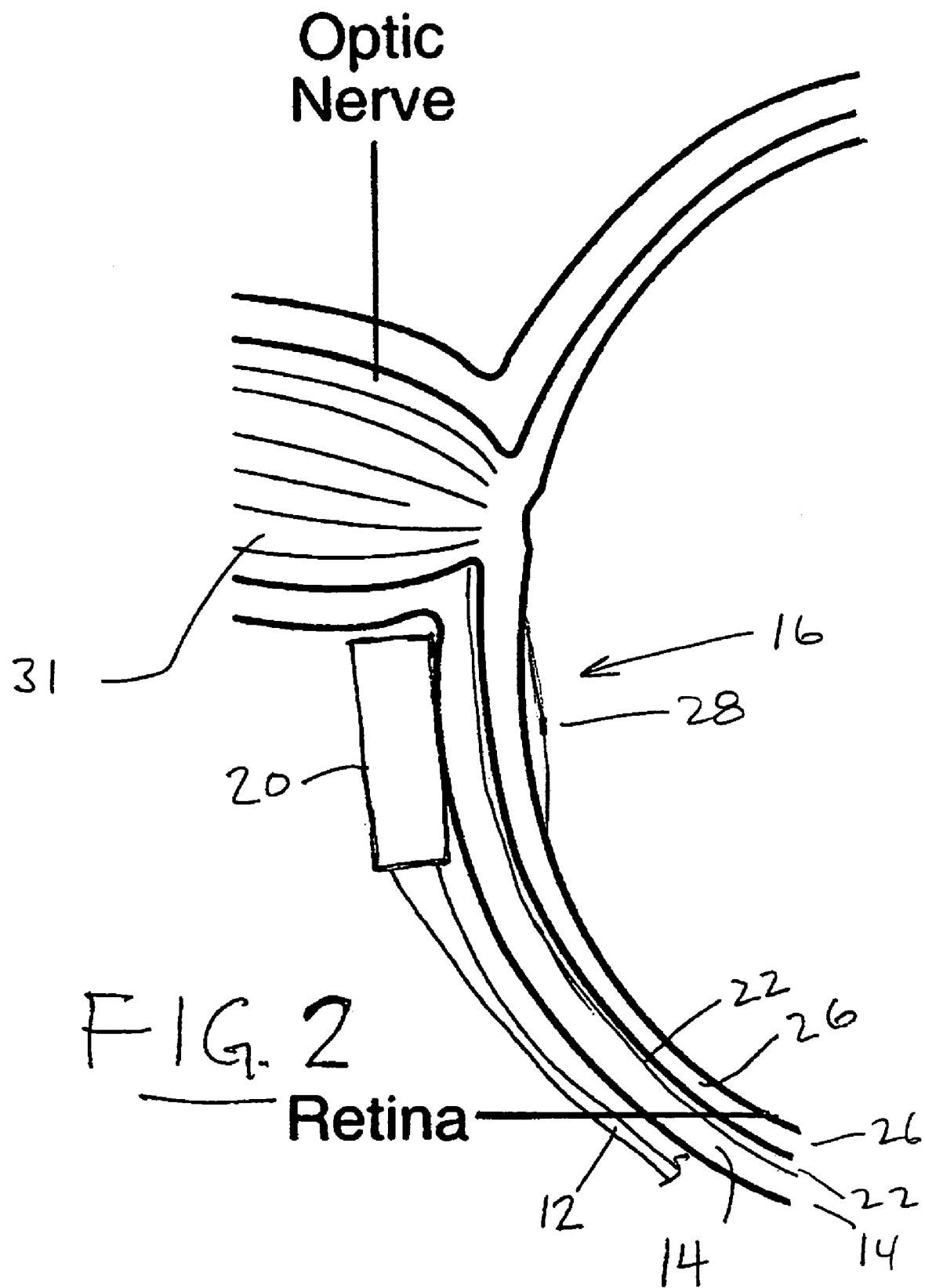
FIG. 2 is an enlarged view in sectional plan showing the catheter or probe of the invention behind the macular region.

FIG. 2 is an enlarged, detailed view, schematic in its illustration of the x-ray source 20. The source 20 is immediately behind the sclera 14, and the source, or the sheath or applicator or guide surrounding the source, directly contacts the back surface of the sclera or contacts a thin layer of fat adjacent to the sclera. As the drawing schematically indicates, the choroid or choroidal membrane 22 is the next tissue layer in from the sclera. The sclera may be about 1 mm in thickness in this region, while the choroidal layer may be only about 0.5 mm thick. Immediately inside the choroidal layer is the retina 26.

The fovea 28 is at the center of the macular region 16, which is typically considered as a region of about 5 to 6 mm in diameter around the fovea (including the foveola, fovea, parafoveal and perifoveal regions). As FIG. 2 indicates, this region is very close to the optic nerve 31, where radiation is to be avoided. The choroidal layer or choroid membrane 22, as explained above, is the region where CNV of age related macula degeneration occurs, and this is the layer, directly behind the macula, to be treated with x-ray radiation according to the invention.

Figure 3:
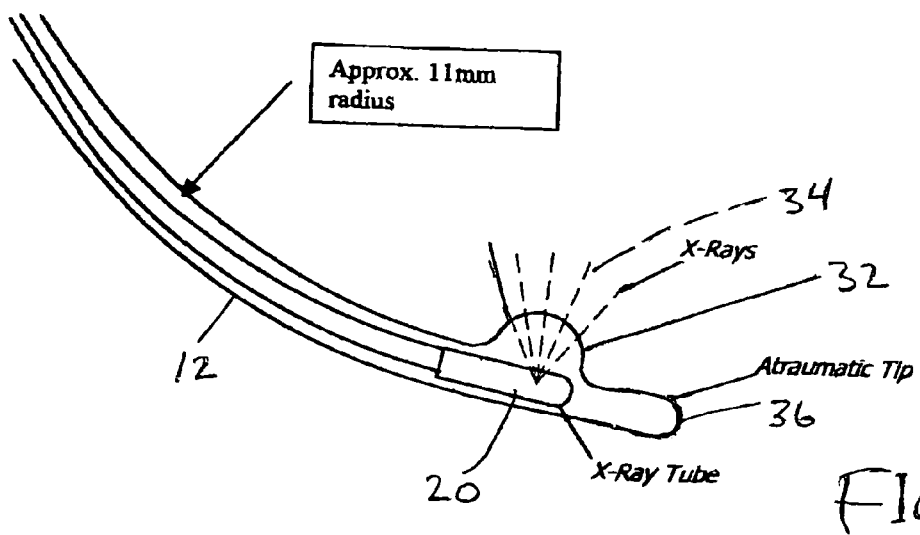
FIG. 3 is a schematic partial plan view showing an embodiment of the catheter of the invention having one type of x-ray source locating means, in this case a protrusion on the surface of the catheter, which also serves as an immobilizer and a standoff to improve radiation surface to depth ratio.

FIGS. 3-8 are concerned with properly locating the probe or catheter 12, and particularly the x-ray radiation, behind the macula. In FIG. 3 one scheme is illustrated for indicating to the physician the location of the x-ray tube behind the retina, and thus allowing adjustment and proper positioning of the probe to approximately center the tube behind the macula. By this arrangement the probe 12 containing the x-ray tube 20, i.e. the exterior of the apparatus inserted around the globe of the eye (which can be a guide), has a "bump" or protrusion 32. This protrusion 32 which can be considered as exaggerated in relative size in FIG. 3, forms a moving ridge or bump in the retina, which is visible to the physician using an optical instrument from the front of the eye. As seen in the schematic view of FIG. 3, the bump 32 preferably is centered over the anode of the x-ray tube 20, i.e. the portion of the tube from which the x-rays 34 originate. In FIG. 3 the end of the probe 12 is shown as round, in atraumatic type 36.

Figure 3A:
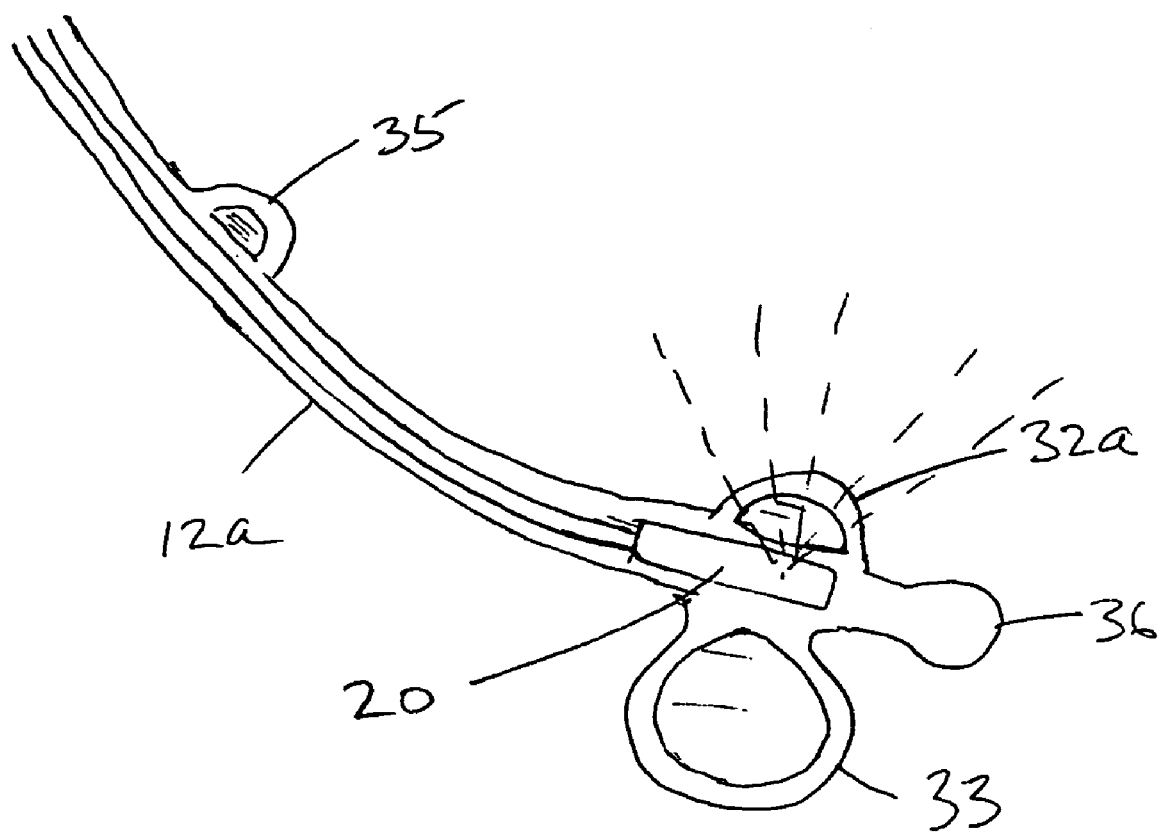
FIG. 3A is a view similar to FIG. 3, showing an inflatable protrusion on the catheter or probe, and also showing additional inflatable balloon devices for immobilization.

FIG. 3A shows a variation of what is shown in FIG. 3. In both FIGS. 3 and 3A, the bump 32 or 32a forms an immobilizing function as well as the locating function described above. The bump 32, 32a pushes against the sclera and thus tends to wedge the probe device more tightly between the sclera and adjacent tissue. Further, this bump 32, 32a serves to stand the radiation source 20 off from the sclera and choroid layers, thus improving surface to depth ratio for the emitted radiation. In FIG. 3A the bump 32a is inflatable, via a lumen (not shown) in the catheter 12a, and the amount of inflation can be varied as needed. This standoff distance is correlated with the voltage setting for the tube 20, thus enabling the physician to optimize x-ray radiation dose in the choroid while minimizing dose in the retina and in the sclera. FIG. 3 also shows an additional inflatable balloon protrusion 33 which can be located on the opposite side of the probe device from the radiation side. This balloon 33, also inflatable via a lumen or duct (not shown) in the catheter 12a, like the bump 32a, is deflated when the probe is inserted. It can be inflated to a selected inflation for helping immobilize the probe after the tube has been properly located behind the macula. Also shown in FIG. 3A is a third inflatable balloon structure 35 which can be included at a selected location along the length of the catheter 12a, to further immobilize the probe and to isolate the catheter tip and x-ray source from movements of the catheter at the proximal end after properly locating the probe. Again, the balloon 35 is deflated during insertion.

Vacuum, i.e. suction against tissues, can also be used to immobilize the device after it is properly located. Suction can be applied through a separate lumen (not shown) in the catheter, and can be applied via openings on the protrusion 32a or 33, spreading the suction over a relatively wide area.

Figure 4:
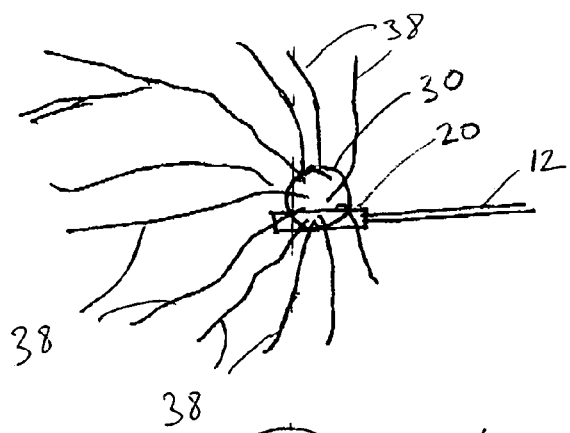
FIG. 4 is a schematic view as seen from the front of the eye and showing the macula and surrounding blood vessels and also revealing the x-ray source of the invention positioned behind the macula (which would actually not be visible through the eye), in this case showing incorrect positioning of the x-ray source.
Figure 5:
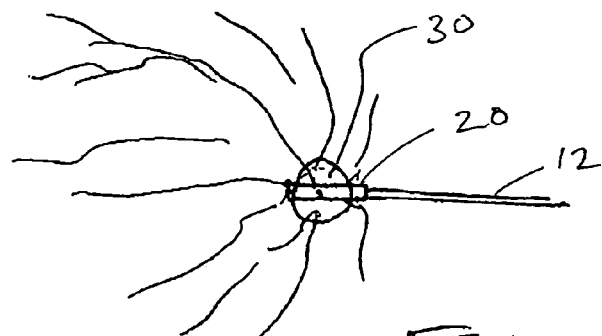
FIG. 5 is a view similar to FIG. 4, but showing the x-ray source correctly positioned behind the macula.

FIGS. 4 and 5 are schematic, relative to the procedure of properly locating the x-ray tube 20 behind the macula (it actually would not be visible from the front of the eye). FIG. 4 shows an example of incorrect positioning of the probe. Blood vessels to the macular region are indicated at 38 in this drawing.

Figure 6:
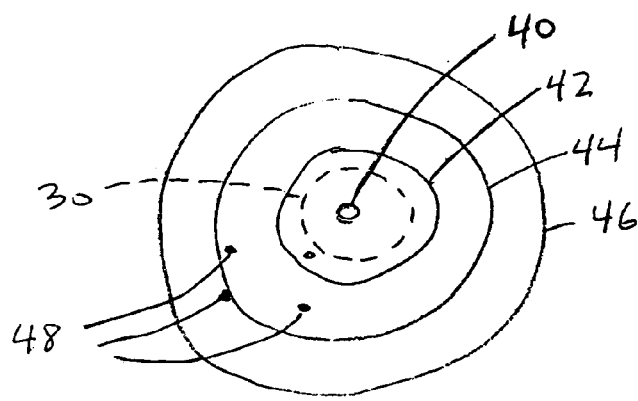
FIG. 6 is a schematic view showing expanding rings of light shone in from the front of the eye, as another method and device for properly locating the x-ray source behind the macula.
Figure 7:
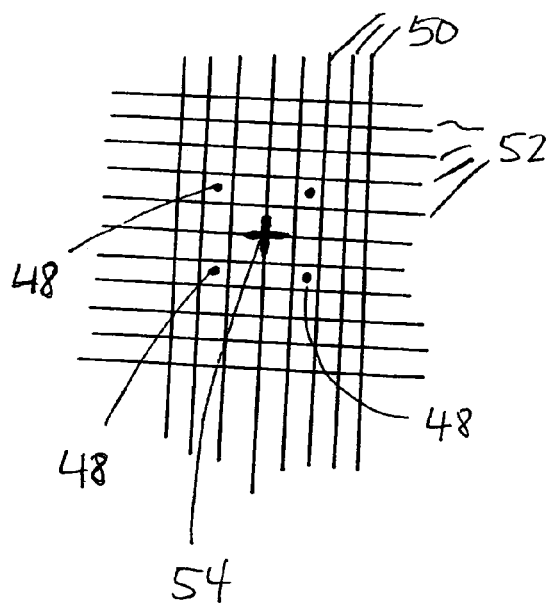
FIG. 7 is a schematic view showing a grid of light lines which can be sequentially activated and detected from sensors on the probe or catheter device, as another means and method for properly locating the x-ray source.
Figure 8:
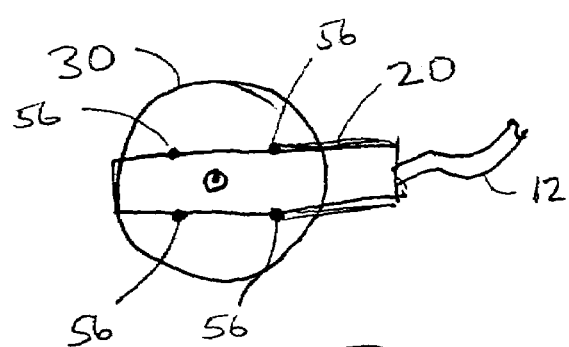
FIG. 8 is a schematic view indicating light sources mounted on the catheter or probe device as another alternative for properly locating the x-ray source behind the macula.
Figure 14:
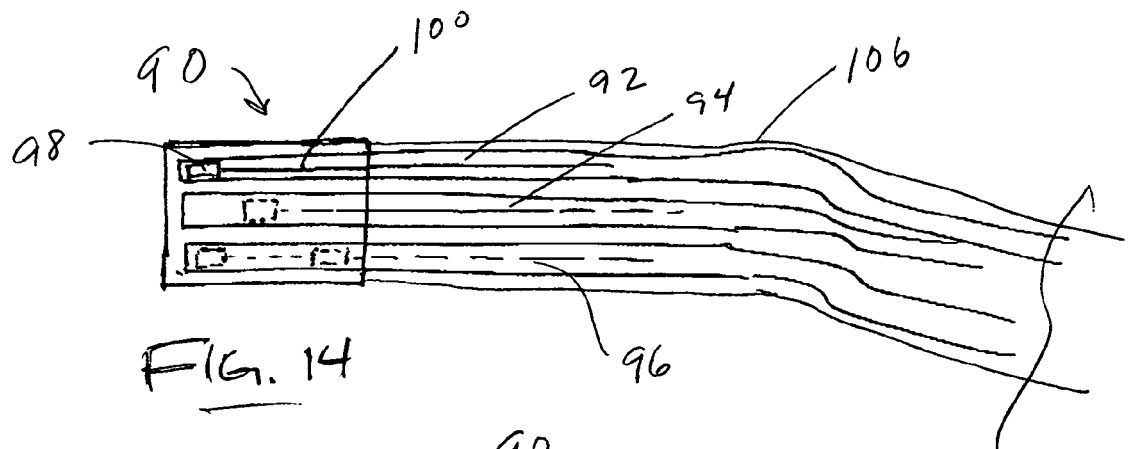
FIG. 14 is a view showing another embodiment in which a guide device or applicator with multiple guide channels is first inserted behind the eye, and the probe with x-ray source is inserted into the guide channels serially to deliver a more evenly distributed dose to the region where needed.

FIG. 5 is similar to FIG. 4, but shows the probe 12 and x-ray tube 20 correctly positioned behind the macula 16. FIGS. 6, 7 and 8 show examples of optical methods and means by which this can be achieved.

In FIG. 6 is shown a series of light rings 40, 42, 44 and 46. These are directed in from the front of the eye, centered on the macular region which is shown at 16 in FIG. 6. The centering of the rings is done by the physician, using an instrument at the front of the eye. The light rings, 40, 42, etc. are constantly expanding (and reappearing at center). Behind the retina is the probe, with a plurality of sensors 48 (in this case four) mounted on the device and preferably centered around the x-ray emission point of origin. These sensors 48 detect the passing of each ring of light 40, 42, 44 and 46 as it expands. Even though the light rings will be considerably scattered as they pass through the partially translucent retina, choroid and sclera to reach the sensors 48, their peak intensities will be detectable at each point 48. Thus, as the rings expand the timing of each peak detection by each of the sensor points 48 is fed to a console (not shown) connected to the probe instrument, and from this information the location of the sensors relative to the center point of origin of the light rings can be determined. When centered the detectors 48 will all detect light peaks simultaneously. Accordingly, an instruction can be generated to the physician as to what direction the probe should be moved in order to achieve correct positioning, or the position of the probe relative to the macula can actually be displayed on a screen on or connected to the console. A robotic device can be used to position the probe, with robotic feedback from the sensors 48 and console.

FIG. 7 shows another probe-location method and system. By this method, a grid of light lines, e.g. vertical light lines 50 and horizontal light lines 52, are generated by an instrument which directs the light in from the front of the eye. The four sensor points 48 discussed with respect to FIG. 6 are shown behind the grid of lines. FIG. 7 is only schematic, and the line spacing in the grid is sufficiently small that light from at least one light line will always be detected by at least some of the plurality of sensors 48 mounted on the probe device. As discussed above, this light will be highly scattered after passing through the retina, choroid and sclera, but its peaks will be detectable. The grid of lines 50, 52 is located by the physician as accurately as possible relative to the macula of the eye, as by a special, distinctively illuminated location intersection 54. The light lines can be sequentially activated, so that the feedback from the sensors 48 will always identify which line of light was detected and by which sensor or sensors. This will give enough information to tell the physician (or a robotic probe manipulator) where the probe is located, and which direction and how far to move it in order to make it properly located behind the macula.

Alternatively, the grid shown in FIG. 7 can represent scanned light lines moving across the retina (fewer lines are needed). By temporal synchronization, the location of each light line at any time is known, allowing the sensors and connected logic to locate the probe. Note that only two, or even one sensor 48 is sufficient for this form of scan locator.

FIG. 8 shows another scheme for properly locating the x-ray tube 20 behind the macular region 16. This arrangement is somewhat similar to that of the Finger patent discussed above, in that light sources 56 are mounted directly on the probe. Four are shown in FIG. 8. In the invention, however, these light sources are angularly cleaved optical fiber ends which receive light from an illumination source in the console. The fiber ends 56 are sufficiently bright that the physician can see the pattern of these light sources behind the macula, and can locate the probe accordingly. The fiber ends may be angularly cleaved, or polished and redirected by reflectors (microprisms).

Another method for indicating and confirming position of the x-ray source behind the eye is to provide a means of seeing the x-ray radiation itself, or seeing evidence of the x-ray radiation, by looking into the front of the eye. This method could involve fluorescence, of a casing or guide device around the x-ray source, or of a medically acceptable substance put into the blood stream, which substance fluoresces when absorbing x-ray radiation. Such a substance could be injected into the intraocular space.

Another way of producing a fluorescing indicator is to use the x-ray tube itself or a transmissive plate or coating on the x-ray tube, as a substance which will fluoresce when struck by x-rays. The applicant has found that sintered aluminum nitride will fluoresce when excited by x-ray radiation.

The x-ray therapy of the invention can be used in conjunction with photodynamic therapy, as mentioned above. By using the two therapies simultaneously (or closely in time to one another), the disruption caused by PDT can be synergistically complemented by radiation therapy. PDT essentially causes a disruption of the capillaries of the choroid layer by a photoactive chemical substance as explained in U.S. Pat. No. 6,548,542 (col. 4, l. 61-col. 5, l. 4), incorporated herein by reference. The photo-activated substance is thought to break down cellular structures and other effects as noted in the '542 patent, resulting in occlusion of the CNV vasculature. X-ray radiation delivered in conjunction with PDT can help remediate AMD in two ways: first, the direct effect is to disable rapidly dividing cells, thus reducing the population of cells which can cause the problem by growing new inappropriate vessels (CNV), and secondarily, the radiation assists in the effects of the PDT by preventing the repair response which naturally follows the PDT treatment.

The invention also encompasses use of radiosensitizing substances in the blood vessels to enhance their sensitivity to radiation. This is the subject of copending application Ser. No. 09/851,372, filed May 7, 2001, assigned to the assignee of the present invention. That copending application is directed primarily at a combination of radiation and radiosensitizer delivery devices to inhibit hyperplasia following balloon angioplasty. The application discloses radiosensitizers such as taxol, misonidazole, metronidazole, etanidazole, 5-fluorouracil, texaphyran, C225 (an anti-EGFR monoclonal antibody), and cyclooxygenase-2 inhibitor. In the present invention, a radiosensitizer such as one of these substances is put into the blood in an effective amount to sensitize the cells in the choroid layer such that a lower dose of x-ray radiation via the probe of the invention can be administered.

Figure 9:
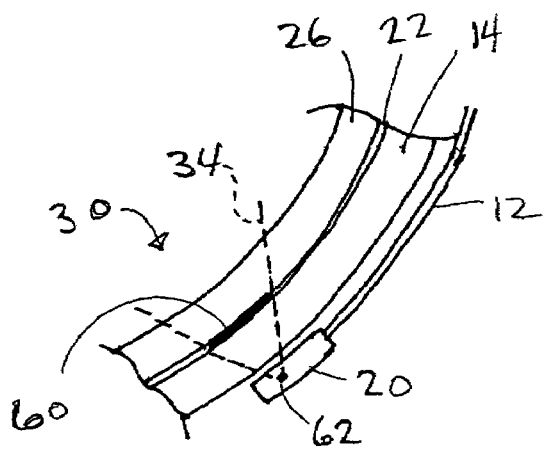
FIG. 9 is a schematic view showing, in a primarily plan view, a limited radiation pattern emitted from the x-ray source and treating the choroid layer behind the macula.

FIG. 9 is a simple schematic showing the x-ray source 20 at the distal end of the catheter or probe 12 and properly located behind the macular region 16 of the eye. The portion of the choroidal layer 22 to be irradiated, i.e. the choroid directly behind the macula, is indicated at 60. The x-ray radiation is shown in a diverging pattern at 34, emanating from a source (the anode) 62 in the x-ray tube, at the proper angle to irradiate the region of interest 60 in the choroid. FIG. 9 shows adjacent structures are irradiated, including the sclera 14 and the retina 26. An approximate dose to depth curve is shown in FIG. 13. The sclera necessarily receives more radiation than the other structures, but the sclera comprises relatively quiescent cells which are not rapidly proliferating, and the radiation dose is not so excessive to cause a problem. The next layer is the choroid with the CNV condition of macular degeneration. This region receives sufficient radiation to provide therapeutic benefit to the patient. Beyond the choroid 22 is the retina 26, which receives a still smaller dose. Regions deeper toward the front of the eye, including the lens and cornea (not shown), receive progressively less dose. With proper selection of voltage filtering and stand-off the switchable x-ray source can deliver considerably less radiation to structures distal to the target tissue (choroid) than current isotope plaque treatment. No radiation damage has been seen in patients treated with plaques with up to 7 years follow-up.

Figure 10:
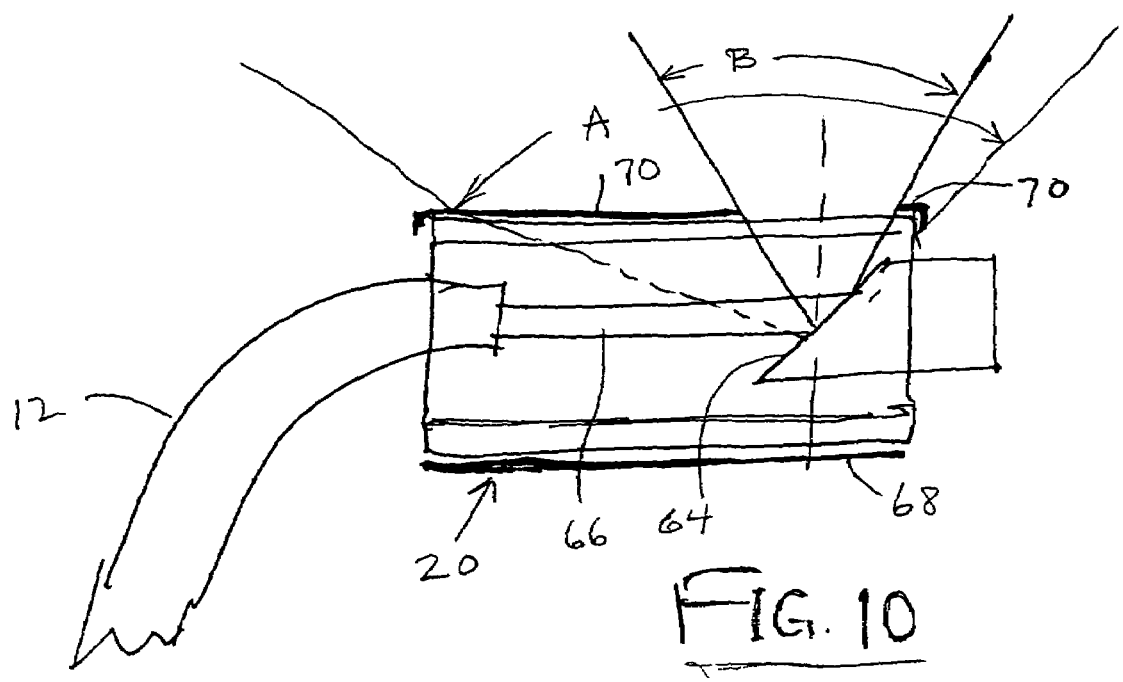
FIG. 10 is a schematic plan sectional view showing an x-ray tube for side-looking, directional radiation.

FIG. 10 schematically indicates an anode construction for the x-ray tube 20, for achieving side-looking, directional emission. In this arrangement the anode comprises an angled face 64, i.e. at approximately 45° (from 22° to 60°) to the direction of the approaching electron beam 66, so that emission is essentially through an arc A. However, the x-ray tube 20 is shielded, as shown at 68 around the preferably cylindrical tube, so that only a desired window 70 of side-looking radiation is emitted, through a desired angle B. The arc of radiation is limited in two dimensions, thus producing radiation which can be an approximate cone. The geometry of the tube and its shielding are selected so that, with the distance from the anode to the choroid layer known, and the width or diameter of the choroid behind the macula known, the correct angle of radiation is emitted. Shielding alone can be relied on to produce the side-looking radiation desired from an x-ray source without an angled anode. Shielding can also be used with an isotope, as noted above.

FIG. 11 is a simplified schematic view showing a "keyed" arrangement for proper rotational orientation of the x-ray source within the catheter or an immediately surrounding sheath 72. The x-ray tube or source 20 has a ridge or protrusion 74, which fits within a complementary channel 76 within the sheath 72 or probe. In the case illustrated, the immediately surrounding structure is a sheath 72 having cooling channels 78, 80, etc. This may be surrounded by a guide 82 shown in dashed lines, and the sheath 72 itself may be keyed for proper rotational orientation within the guide 82. A keyhole shape such as illustrated with the tube 20 is not needed; a simple, small elongated ridge or a shorter bump, or a non-round shape such as elliptical will suffice to provide orientation. It is imperative that the side-looking x-ray device be properly oriented to direct the radiation toward the choroid region to be treated. This can be achieved by many different arrangements.

FIG. 12 shows an alternative method for irradiating the CNV affected choroid region, shown at 84 in this simple schematic. The optic nerve 31 is shown in FIG. 12 but is behind the plane of treatment in which are located the probe 12 and the treatment region 84. In this case the x-rays 86 are directed generally tangentially to the eye, or chordally, as illustrated. This is a method for avoiding any significant radiation to the retina, indicated at 26, by passing the radiation essentially tangentially or chordally through the sclera and a part of the choroid, to the region of CNV directly behind the macula. The x-ray source tailored to produce a flat beam of the appropriate width and direction. Distances in FIG. 12 are neither to scale nor proportional.

Figure 15:
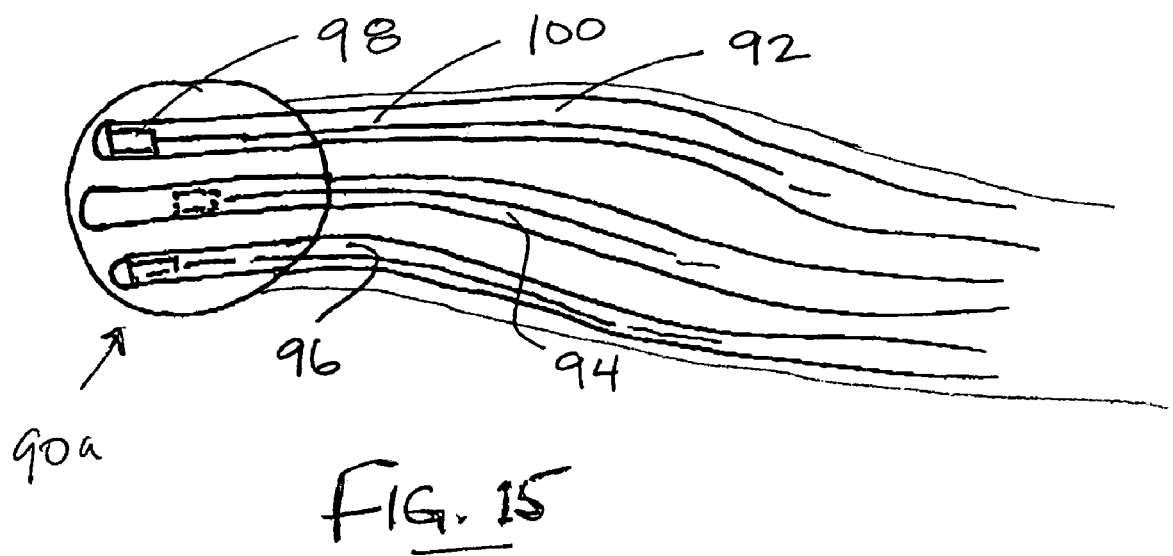
FIG. 15 is a view similar to FIG. 14, but with the probe having a different end shape.

FIGS. 14-18 show another embodiment of the invention, wherein a guide device or applicator 90 or 90a has a plurality of parallel guides or channels 92, 94 and 96 for receiving the insertion of a probe 98 with an x-ray source and attached cable 100 (FIG. 15 shows an applicator 90a with a different, more rounded shape). In this case the applicator 90, 90a is flat in thickness and relatively wide, ribbon-like in shape, to accommodate the multiple channels, three in one preferred embodiment. For example, the applicator or guide device can be about 4½ mm in width and about 1½ mm in thickness, although the eye could accommodate considerably greater thickness.

As noted above, the multiple channels or guides allow an x-ray source, which can be either a switchable x-ray tube or an isotope, to be indexed to a number of different dose delivery positions within a grid or matrix of positions, thus enabling a more evenly distributed dose to the macular region, and allowing better control of the distribution of radiation. Translation of the radiation source behind the sclera to multiple positions for dose delivery reduces the dose to the sclera while maintaining the desired dose to the macula. Comparison can be made to the first embodiment, FIG. 3 or FIG. 9 for example. By distributing the positions from which radiation dose is delivered, this multiple-channel embodiment reduces concentration of radiation dose in a particular zone of the sclera as would occur by delivering all dose from a single position, in a fanning-out pattern of radiation (as in FIG. 3 or FIG. 9).

The positions at which the radiation dose is delivered could be stepped in a pattern such as a 3×3 grid, or with continuous pullback in each guide channel. This could be done for isotopes as well as for switchable x-ray sources. The applicator 90, 90a acts as a guide device with several channels or guides within the region of interest. The entire guide assembly can be thin and compact to allow insertion and positioning. If desired the guide assembly can be shrunk smaller for insertion then subjected to fluid pressure that expands the guide to provide lateral separation for the channels or guide tracts, tracks after positioning.

The source guides or channels 92, 94, 96 are essentially linear, except to curve around the exterior of the eye, and they allow either stepped treatment or continuous pullback. The plurality of parallel guide channels are relatively close to each other, such as a few millimeters spacing at centers. A larger separation could also be used, where the guide channels are positioned farther apart and the source could be rotated appropriately in each channel to point toward the macula. A keyway in each guide (92, 94, 96) can be provided to orient the source correctly toward the macula, the orientation being different in each channel.

Figure 16:
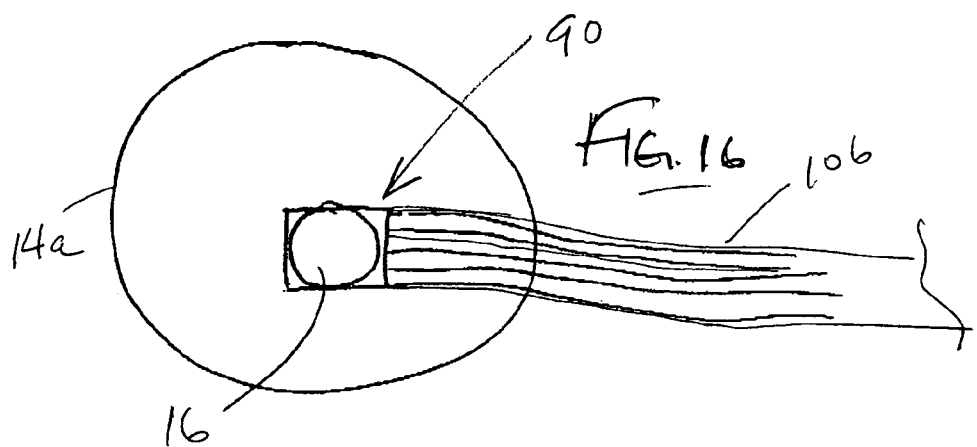
FIG. 16 is a frontal view relative to the eye, somewhat similar to FIG. 5, showing the applicator of the invention as inserted in correct position behind the macula.

FIG. 16 schematically indicates the multi-guide applicator 90 in accurate position behind the macular region 16, with the outline of the globe of the eye itself, i.e. the sclera, being indicated at 14a. Location techniques and apparatus can be used as described above, including techniques and arrangements shown in FIGS. 3 through 8, and the accompanying discussion above. For example, optical light sources can be used to assure that the radiation source is properly positioned relative to the target for each stepwise position or to begin a pullback procedure.

Figures 17, 18:
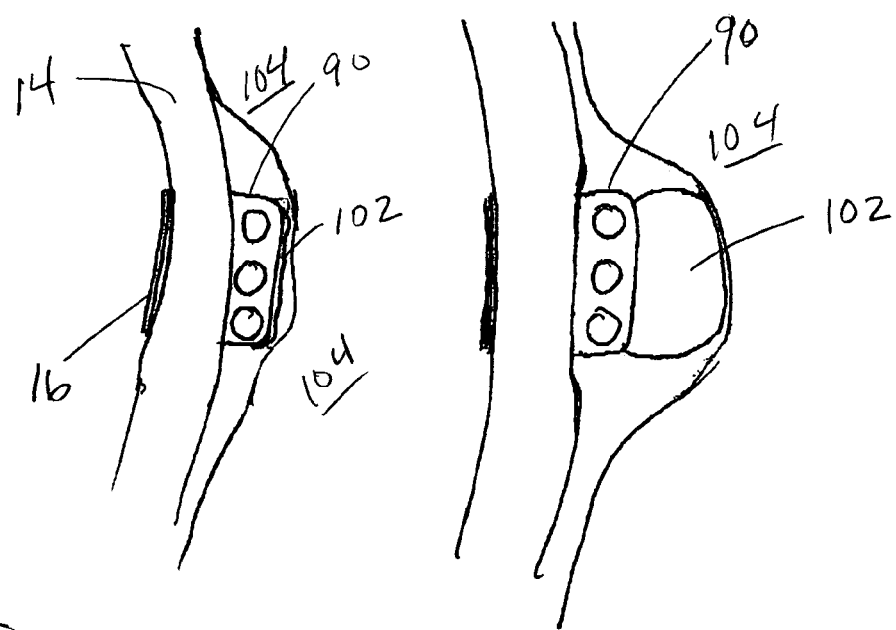
FIGS. 17 and 18 are a side cross sectional views, somewhat similar to FIG. 2, schematically showing a portion of the macula of the eye and indicating the multi-channeled applicator of the invention as inserted behind the sclera in this region. The probe includes an inflatable balloon, shown inflated in FIG. 18 to press the probe against the back of the sclera.

FIGS. 17 and 18 show a form of the applicator device 90 with a balloon 102 attached to an outer side. The sclera is shown at 14, the targeted macular (choroid) zone at 16. The device 90 is indicated as inserted between the outside of the sclera 14 and tissue 104 behind the eye. In FIG. 17 the balloon 102 is deflated, and in FIG. 18 the balloon is inflated. This pushes the multi-tract guide device 90 firmly against the back of the sclera (or against an intervening fat layer) and effectively immobilizes the device 90 for the treatment. For this purpose a small balloon inflation channel or lumen (for liquid or gas) is provided in the ribbon-like applicator cable or line 106 (inflation lumen not shown in FIGS. 17-18).

If a prescription radiation dose is delivered to the macula from a single position (as in FIGS. 1-5 above), in a cone-like pattern, the dose to the first wall (sclera) encountered by the radiation is quite high. If, on the other hand, the source is moved through three guide channels, and dwells at (for example) three locations within each guide, the dose at any particular area of the sclera will drop by a significant amount, which could be a factor as large as about ten for central regions of the sclera. If, as an example, the source catheter in the earlier embodiment is 1 mm in radius and the macula is a distance of 1 mm through the sclera, and the prescription dose to the macula is 15 Gy, then the dose to the sclera is at least 60 Gy based soley on $1/r^2$ with attenuation in the tissue, the dose would be higher at the sclera surface. With multiple-guide channel translation, on the other hand, the dose to the sclera can be reduced to 6 Gy plus the overlap dose which depends on the guide channel separation. Continuous pullback tends to be better than stepped positioning for reducing the dose to the sclera. For example, with two guides and two positions per guide, a 2×2 matrix is produced with about ¼ the dose delivered to critical regions of the sclera; with three guides and three positions the dose to critical areas can be about ⅑; and with a 4×4 matrix the dose concentration is reduced even further, with the limitation as positions increase that overlap increases and the benefit begins to drop off. Continuous pullback is best for this reason, eliminating overlap in the one direction of the matrix.

Isotopes can be used with the multiple-guide channel device described above. A probe or catheter with an isotope can deliver a prescription dose by pullback at a prescribed rate in each of the multiple guide channels in succession, the probe being withdrawn and inserted at a very rapid rate through the guide channels between and after applications. If desired, however, shielding can be used. In one form, the end of each guide can comprise a shield, which will be positioned just beyond the region to be irradiated. In another form of shielding, the probe can include a shield that is deployable by manipulation at the exterior site of the device, to avoid any radiation to regions not to be treated.

The applicator described above can be produced of a biocompatible material, such as medical grade silicone, HYTREL or PEBAX marketed by Dupont, or other similar materials.

The applicators shown in FIGS. 14-18 can advantageously be provided with guides keyed to the cross sectional shape of the catheter, a non-round shape that will assure the correct rotational orientation of the catheter to emit directional radiation to the desired target. The applicator's guides can accommodate more than one possible rotational position for the catheter if desired, by including two or more keyways within which a key or bump in the cross section of the catheter is positioned and slides. This provides a way of assuring that the radiation is directed appropriately at the target.

The multiple positions of the catheter in each guide or channel can be effected manually, or more preferably, by an automated and programmed device. The catheter, whether it carries a switchable x-ray tube or an isotope, can be moved in steps or continuously within an applicator guide, and can be rotated to different rotational orientations, if desired, in accordance with a program. If the catheter is used without an applicator, the x-ray source can be manipulated in X and Y directions, and also rotationally, if desired, using a similar programmed device.

Figure 19:
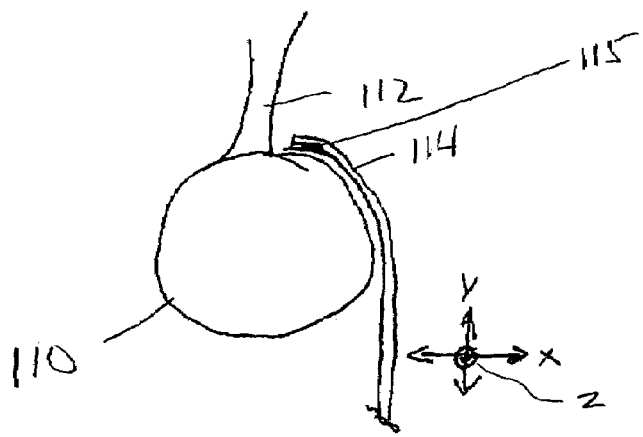
FIG. 19 is a schematic plan view showing the globe of a patient's eye and a probe or applicator inserted around and behind the globe, and indicating freedom of motion for manipulation of the probe behind the macula or the tissue.

FIG. 19 schematically shows an eye 110, indicating the optic nerve 112. The x-ray applicator 114 is shown positioned behind the globe of the eye 110, near the location of the macula. The probe has freedom of motion such that the probe can be moved tangent to the rear of the globe so that the probe can be translated across the macula or translated up and down across the macula (X and Y directions); and it can also have freedom of motion in the Z direction, i.e. posterior or anterior relative to the macula, in/out relative to the back of the globe. This is useful to set the appropriate distance back from the macula, to improve the ratio of dose to the macula as compared to dose at the sclera. This Z-direction movement can be permitted using balloon devices such as shown in FIG. 3A and discussed in the above description. Y-direction movement can also be facilitated in various ways. One method is to have the applicator somewhat ribbon-shaped, generally as in FIGS. 14-18 but possibly even more exaggerated in dimensions of the width compared to the thickness, so that the surgeon can manipulate the applicator in the Y-direction from outside the eye. Another method is to have a "kink" in the applicator, somewhere proximal to the end, so that rotation of the applicator (which in this case will not be so ribbon-like) will have the effect of raising or lowering the applicator tip relative to the macula.

Figure 20:
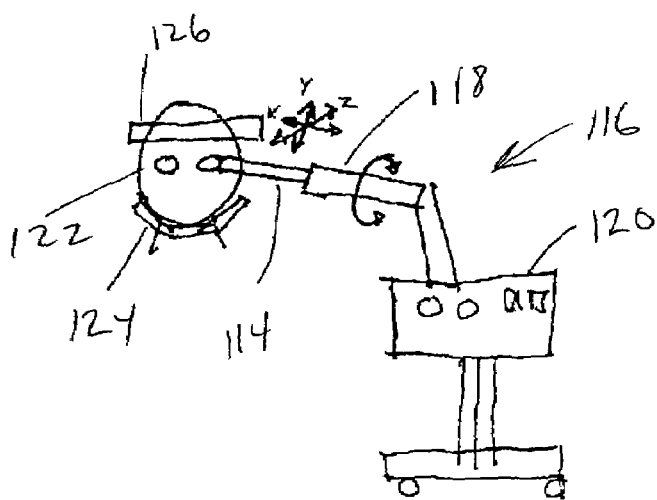
FIG. 20 is a schematic view in elevation, showing an automated system for manipulation of the positions of the probe behind the patient's eye.

FIG. 20 shows an automated translation device 116, with an articulated arm 118 extending from a console 120 and supporting the applicator 114 and the probe with the x-ray source, not shown in FIG. 20, for manipulation within the applicator. The patient 122 is indicated with the probe inserted around the globe of the left eye, the probe being within the applicator 114. The patient's head is positioned in a frame, indicated at 124 and 126, to ensure that the head does not move relative to the arm 18 and the probe. The manipulator arm 118 is indicated as having X, Y and Z degrees of freedom, as well as an additional degree of freedom, rotation of the arm about its longitudinal axis, for rotation of the x-ray probe. The movements of the arm are controlled by the console 120, in accordance with a computer program that defines the procedure to be carried out. The X, Y and Z motions can be carried out using methods such as described as above. X-direction motion is a simple in/out movement of the applicator 114 relative to the arm 118. Y-direction movement can be achieved by the mechanical device 116 by manipulation of the ribbon-like shaped applicator as discussed above, or by a rotation of a narrower applicator, using a "kink" in the applicator to effect Y-direction movement as a reaction to the rotation. For this purpose, inflatable balloons around the applicator's position can be used to spread the tissues to allow such movement.

Inflatable balloons could be used in other ways, positioned adjacent to the applicator tip, to effect Y-movement. Z-direction movement can also be achieved using balloons for manipulation of position, as discussed above.

The applicator as positioned and manipulated by the automated translation device 116 can include a single guide channel for the catheter having the radiation source, or it can be without guides, simply manipulating the catheter in an appropriate configuration to permit such manipulation. It should also be pointed out that Y-direction movement, if desired, could be achieved with the translation device 116 in connection with a multiple-guide channel applicator such as shown in FIGS. 14-18, with the device 116 pulling back the catheter and moving it into different guide channels to achieve the difference in Y position during treatment.

Figure 21A:
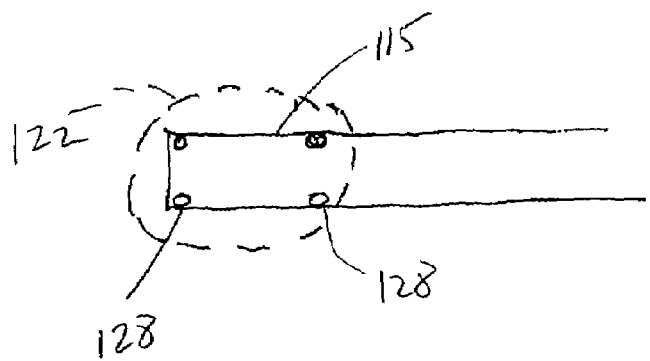
FIGS. 21A and 21B are schematic elevation views to indicate detection of correct and incorrect positioning of the probe behind the eye, as determined by light sensors on the probe.
Figure 21B:
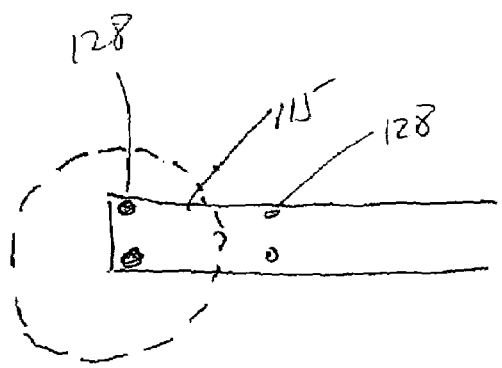
Figure 23:
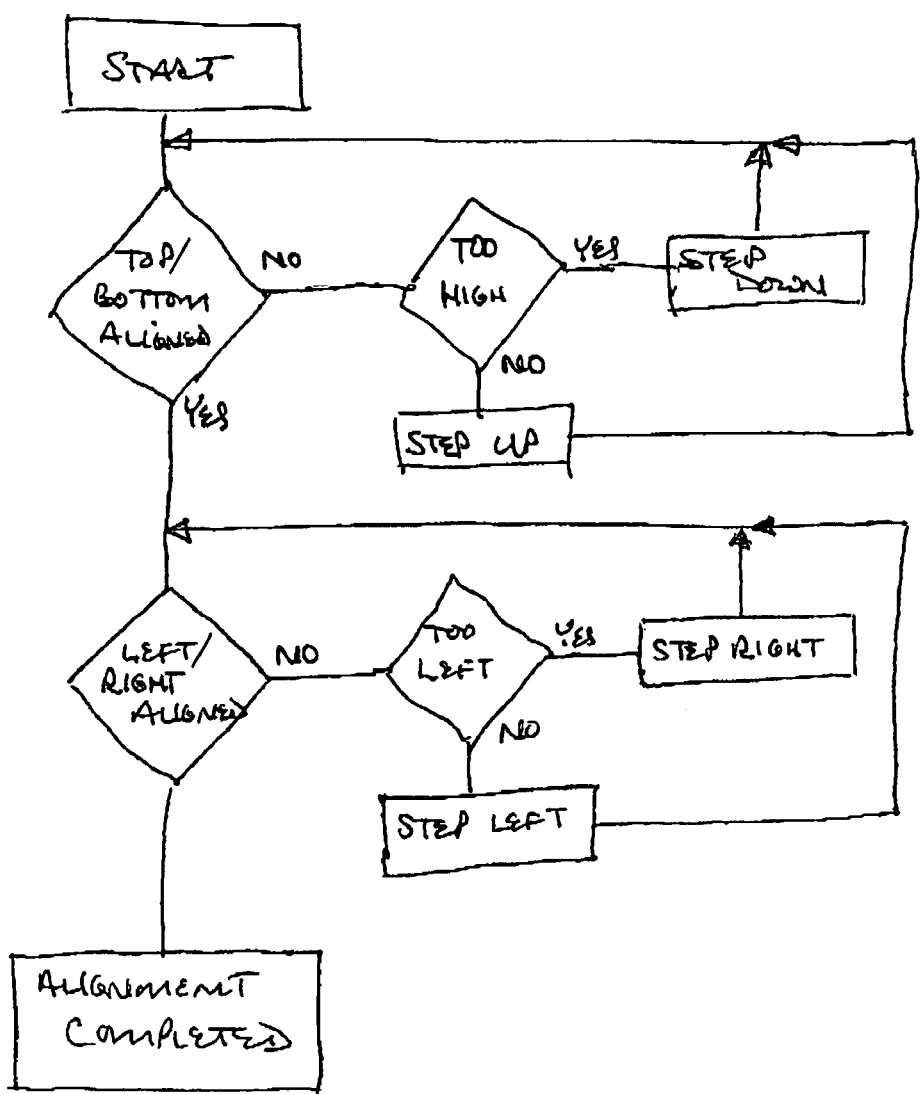
FIG. 23 is a simple flow diagram indicating procedure for achieving the correct position.

FIGS. 21a and 23 show a system to achieve correct positioning of a probe or applicator or catheter behind the eye. In FIGS. 21a and 21b the probe 115 is schematically shown behind the globe of the eye, and an alignment system is indicated that utilizes light sources. In FIG. 21a the probe is correctly positioned behind the eye 122, and in FIG. 21b it is not correctly positioned. In this example the alignment light is directed into the eye from the front of the eye, and is detected by a plurality of sensors (e.g. four) on the probe, shown at 128. The sensors 128 detect the light and relative values of the light in such a way as to determine where the probe is positioned at any time, and the programming determines the correctional position needed.

Figure 22:
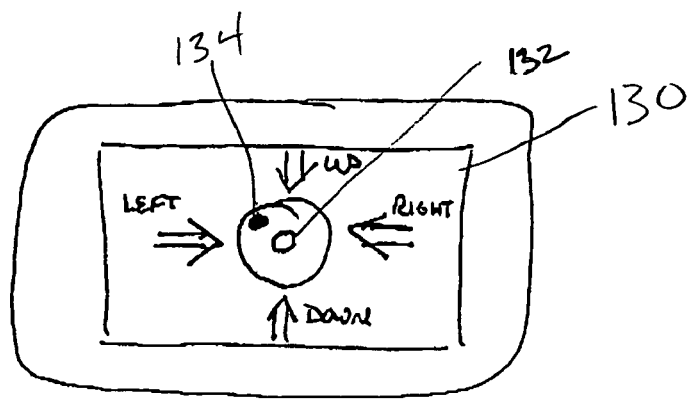
FIG. 22 is a view showing a monitor screen to indicate detection and correction of positioning of the probe behind the eye.

In FIG. 22 a monitor screen 130 shows the position of the probe relative to the alignment beam. The alignment beam position is indicated at 132, with the probe indicated by the black dot at 134. The direction arrows on the monitor show the direction the probe should be move to align the probe with the macula. When the probe is correctly positioned, the dot will be inside a circle 132 in the center of the monitor. The positioning of the probe preferably is done automatically, but the monitor 130 can be provided to indicate to the physician the process of alignment, or the monitor 130 can be used in a manual procedure wherein the physician positions the probe through manipulation of the probe or the applicator.

FIG. 23 is a simple flow chart indicating the automated positioning system. The system automatically examines the position of the probe using the sensors and steps the probe to bring all sensors into balance. There are many additional steps not specifically shown, including safety steps such as limiting the motion to various small steps, shutting down the system if sensor data is lost, shutting down if more than a safe distance is traveled, etc.

The apparatus and method of the invention also can be used to treat ocular tumors or tumors adjacent to the globe of the eye, with radiation. The same catheter is used, (with or without a guide device), with a switchable source, for tumors at different locations in the ocular tissue. The source preferably is a directional source, and correct rotational orientation can be assured with a pre-inserted applicator that has a cross sectional shape keyed to that of the catheter.

The above described preferred embodiments are intended to illustrate the principles of the invention, but not to limit its scope. Other embodiments and variations to this preferred embodiment will be apparent to those skilled in the art and may be made without departing from the spirit and scope of the invention as defined in the following claims.

We claim:

1. A method for treating AMD, comprising:
    sliding a catheter around the globe of the eye of a living patient, the catheter containing a switchable x-ray source capable of directional emission in a distal end of the catheter, to a position behind the macular region of the retina,
    properly locating the catheter behind the macular region by activating one or more light sources on the catheter, and viewing the light sources using an optical instrument from the front of the eye, the light sources being visible through the sclera, choroid and retina, and
    switching on the x-ray source to emit directed radiation through the sclera into the choroid membrane.

2. The method of claim 1, wherein the light sources at the catheter comprise optical fibers receiving light from a source of illumination at a console to which the fibers are connected.

3. The method of claim 2, wherein the optical fibers have angularly cleaved ends as said light sources at the catheter.

4. The method of claim 2, wherein the optical fibers are polished and wherein the light sources at the catheter include micro prism reflectors directing light from the optical fibers toward the front of the eye.

5. A method for treating AMD, comprising:
    sliding a catheter around the globe of the eye of a living patient, the catheter containing a switchable x-ray source capable of directional emission in a distal end of the catheter, to a position behind the macular region of the retina,
    properly locating the distal end of the catheter behind the macular region by directing a preselected pattern of light toward the retina from the front of the eye, and detecting the pattern of light using detectors located near the distal end of the catheter, in such a way as to indicate a direction of movement for correction of the catheter's position, and
    switching on the x-ray source to emit directed radiation through the sclera into the choroid membrane.

6. The method of claim 5, wherein the pattern of light comprises repeated expanding rings of light.

7. The method of claim 5, wherein the pattern of light comprises a grid of light lines illuminated sequentially.

8. The method of claim 5, wherein the pattern of light comprises a color gradation pattern, with color indicating location.

9. The method of claim 5, wherein the pattern of light comprises a moving pattern of light and the method includes temporally sensing the position of the catheter by reference to the moving pattern.

10. A method for treating AMD, comprising:
    sliding a catheter around the globe of the eye of a living patient, the catheter containing a switchable x-ray source capable of directional emission in a distal end of the catheter, to a position behind the macular region of the retina, the switchable x-ray source comprising a miniature x-ray tube emitting a side-looking directional radiation,
    switching on the x-ray source to emit directed radiation through the sclera into the choroid membrane, and including filtering the radiation emitted from the x-ray source to harden the x-ray beam, using one or more filters coated onto the tube or a sleeve over the tube, thus reducing unwanted dose in the sclera.

11. A method for treating AMD, comprising:
    sliding a catheter around the globe of the eye of a living patient, the catheter containing a switchable x-ray source capable of directional emission in a distal end of the catheter, to a position behind the macular region of the retina, and switching on the x-ray source to emit directed radiation through the sclera into the choroid membrane, and including filtering the radiation emitted from the x-ray source to harden the x-ray beam, using one or more filters coated onto the tube or a sleeve over the tube, thus reducing unwanted dose in the sclera.

12. The method of claim 11, wherein the distal end of the probe includes an adjustable standoff device for standing the x-ray source off from the sclera after insertion of the catheter, the x-ray source comprising a miniature x-ray tube, and including the step of selecting and balancing parameters of standoff distance of the source from the sclera and voltage applied to the miniature x-ray tube, to optimize the parameters to achieve a prescription radiation dose in the choroid and to limit dose in the sclera and minimize dose in the retina.

13. A method for treating AMD, comprising:
sliding a catheter around the globe of the eye of a living patient, the catheter containing a switchable x-ray source capable of directional emission in a distal end of the catheter, to a position behind the macular region of the retina,
properly locating the distal end of the catheter by a protrusion in the surface of the catheter, near its distal end, and the method including viewing the retina from the front of the eye as the catheter is inserted, thus observing a protrusion in the retina caused by the protrusion on the catheter, until the catheter is properly positioned, and
switching on the x-ray source to emit directed radiation through the sclera into the choroid membrane.

14. The method of claim 13, wherein the protrusion in the surface of the catheter comprises an inflatable balloon, and the method including inflating the balloon of the protrusion to a selected extent after properly locating the distal end of the catheter to stand the distal end off from the sclera to a desired extent to improve the surface to depth dose ratio.

15. The method of claim 14, further including at least one additional inflatable balloon on the catheter, the additional inflatable balloon, along with said protrusion, serving to help immobilize the catheter after proper location of the distal end of the catheter.

16. The method of claim 14, wherein the x-ray source comprises a miniature x-ray tube, and including the step of selecting the extent of standoff of the x-ray source from the sclera, and selecting a voltage for the x-ray source and optimizing the standoff and the voltage to achieve a prescription dose to target tissue of the choroid and minimize dose to non-target ocular tissue.

17. The method of claim 16, further including filtering the radiation emitted from the x-ray source to harden the x-ray beam, using one or more filters coated onto the tube, thus reducing unwanted dose in the sclera.

18. A method for treating AMD, comprising:
sliding a catheter around the globe of the eye of a living patient, the catheter containing a switchable x-ray source capable of directional emission in a distal end of the catheter, to a position behind the macular region of the retina,
the catheter including a guide having a non-round elongated internal cavity, the x-ray source having a complementary shape fitted to the non-round cavity so as to orient the x-ray tube rotationally within the guide, and the non-round cross sectional shape in the guide comprising generally a keyhole shape or an elliptical shape, and
switching on the x-ray source to emit directed radiation through the sclera into the choroid membrane.

19. A method for treating AMD, comprising:
sliding a catheter around the globe of the eye of a living patient, the catheter containing a switchable x-ray source capable of directional emission in a distal end of the catheter, to a position behind the macular region of the retina,
administering to the patient vascularly a radiosensitizing drug, in an effective amount to sensitize the cells in the choroidal layer such that a lower dose or x-ray radiation can be delivered, and then
switching on the x-ray source to emit directed radiation through the sclera into the choroid membrane.

20. A method for treating AMD in combination with photodynamic therapy administered to the eye, comprising:
sliding a catheter around the globe of the eye of a living patient, the catheter containing a switchable x-ray source capable of directional emission in a distal end of the catheter, to a position behind the macular region of the retina, and
switching on the x-ray source to emit directed radiation through the sclera into the choroid membrane,
and the method including administering a photo-activated substance vascularly to the patient and then photo-activating the substance by directing light through the front of the eye to thereby disrupt CNV vasculature in the choroid layer at the macula, the x-ray radiation serving to disable rapidly dividing cells of the CNV vasculature and to assist in the effects of the photodynamic therapy by preventing a repair response which naturally follows photodynamic treatment.

21. A method for treating AMD, comprising:
sliding a catheter around the globe of the eye of a living patient, the catheter containing a switchable x-ray source capable of directional emission in a distal end of the catheter, to a position behind the macular region of the retina, including properly locating the catheter behind the macular region by exciting a fluorescent substance on the catheter with x-ray radiation from the source, and viewing the fluorescent substance using an optical instrument from the front of the eye, and
switching on the x-ray source to emit directed radiation through the sclera into the choroid membrane.

22. The method of claim 21, wherein the x-ray source is a miniature x-ray tube, and the fluorescent substance being on the tube.

23. A method for treating AMD, comprising:
inserting an applicator around the globe of the eye of a living patient, the applicator having at least one guide channel, and sliding a catheter into the guide channel of the applicator to slide the catheter around the globe of the eye, the catheter containing a switchable x-ray source capable of directional emission in a distal end of the catheter, to a position behind the macular region of the retina, and
switching on the x-ray source to emit directed radiation through the sclera into the choroid membrane.

24. The method of claim 23, wherein the applicator has a plurality of parallel guide channels, and including inserting the catheter into each of the parallel guide channels successively to deliver radiation in a desired distribution, avoiding concentration of radiation in the sclera.

25. The method of claim 23, further including properly locating the applicator behind the macular region by activating one or more light sources on the applicator, and viewing the light sources using an optical instrument from the front of the eye, the light sources being visible through the sclera, choroid and retina.

26. The method of claim 23, wherein the guide channel and the catheter have keyed non-round cross sectional shapes so as to key a desired rotational orientation for directed radiation from the x-ray source when the catheter is positioned in the guide channel.

27. A method for treating AMD, comprising:
sliding an applicator around the globe of the eye of a living patient, the applicator having a plurality of parallel guide channels, to a position behind the macular region of the retina,
verifying accurate positioning of the applicator, and
sliding a catheter containing an x-ray source capable of directional emission through the plural guide channels in succession, to deliver a prescription dose of radiation through the sclera into targeted tissue of the choroid membrane.

28. The method of claim 27, wherein the x-ray source comprises a switchable miniature x-ray tube, and the method including switching the x-ray source on to emit radiation only when the source is in proper position behind the targeted tissue.

29. The method of claim 28, wherein the radiation is emitted in stepwise fashion in a grid of positions by pulling back the catheter to a plurality of dwell positions within each guide channel.

30. The method of claim 28, wherein the switchable miniature x-ray tube is switched on continuously through a continuous pullback routine for a prescribed distance within each of the guide channels.

31. The method of claim 27, wherein the x-ray source comprises an isotope.

32. A method for inserting and correctly locating an applicator having parallel guides by insertion peripherally around the globe of the eye, for therapeutic treatment of the eye, comprising locating the applicator behind the macular region by activating light sources on the applicator, and viewing the light sources using an optical instrument from the front of the eye, the light sources being visible through the sclera, choroid and retina.

33. The method of claim 32, wherein the light sources at the applicator comprise optical fibers receiving light from a source of illumination at a console to which the fibers are connected.

34. The method of claim 33, wherein the optical fibers have angularly cleaved ends as said light sources of the probe or applicator.

35. A method for inserting and correctly locating a therapeutic probe or applicator by insertion around the globe of the eye, for therapeutic treatment of the eye, comprising locating the distal end of the probe or applicator behind the macular region by directing a preselected pattern of light toward the retina from the front of the eye, and detecting the pattern of light using detectors located near the distal end of the probe or applicator, in such a way as to indicate a direction of movement for correction of the position of the probe or applicator.

36. The method of claim 35, wherein the pattern of light comprises repeated expanding rings of light.

37. The method of claim 35, wherein the pattern of light comprises a grid of light lines illuminated sequentially.

38. The method of claim 35, wherein the pattern of light comprises a color gradation pattern, with color indicating location.

39. The method of claim 35, wherein the pattern of light comprises a moving pattern of light and the method includes temporally sensing the position of the probe or applicator by reference to the moving pattern.

40. A method for inserting and correctly locating a therapeutic probe or applicator by insertion peripherally around the globe of the eye, for therapeutic treatment of the eye, comprising locating the distal end of the probe or applicator by a protrusion in the surface of the probe or applicator, near its distal end, and the method including viewing the retina from the front of the eye as the probe or applicator is inserted, thus observing a protrusion in the retina caused by the protrusion on the probe or applicator, until the probe or applicator is properly positioned.

41. A method for treating AMD, comprising:
sliding a catheter around the globe of the eye of a living patient, the catheter containing a switchable x-ray source capable of directional emission in a distal end of the catheter, to a position behind the sclera and not directly behind the macular region of the retina, and including properly locating the catheter behind the sclera in proper position aimed at the choroidal layer by activating light sources on the catheter and viewing the light sources using an optical instrument from the front of the eye, the light sources being visible through the sclera, choroid and retina, and
switching on the x-ray source to emit directed radiation through the sclera into the choroidal layer, in a direction essentially tangential or chordal relative to the globe of the eye, essentially not passing radiation through the retina.

42. The method of claim 41, wherein the light sources at the catheter comprise optical fibers receiving light from a source of illumination at a console to which the fibers are connected.

43. A method for treating AMD, comprising:
sliding a catheter around the globe of the eye of a living patient, the catheter containing a switchable x-ray source capable of directional emission in a distal end of the catheter, to a position behind the sclera and not directly behind the macular region of the retina, the x-ray tube being shielded to provide a desired, limited directional radiation in a tangential or chordal direction relative to the globe of the eye, and including filtering the radiation to be emitted from the x-ray source to harden the x-ray beam, using one or more filters coated onto the tube or onto a sleeve surrounding the tube, thus reducing unwanted dose in the sclera, and
switching on the x-ray source to emit directed radiation through the sclera into the choroidal layer, in a direction essentially tangential or chordal relative to the globe of the eye, essentially not passing radiation through the retina.

44. A method for treating AMD, comprising:
sliding a catheter around the globe of the eye of a living patient, the catheter containing a switchable x-ray source capable of directional emission in a distal end of the catheter, to a position behind the sclera and not directly behind the macular region of the retina, and including properly locating the distal end of the catheter by a protrusion in the surface of the catheter, near its distal end, and the method including viewing the retina from the front of the eye as the catheter is inserted, thus observing a protrusion in the retina caused by the protrusion on the catheter, until the catheter is properly positioned, and switching on the x-ray source to emit directed radiation through the sclera into the choroidal layer, in a direction essentially tangential or chordal relative to the globe of the eye, essentially not passing radiation through the retina.

45. A method for treating a tumor in or adjacent to the eye of a patient, comprising:

inserting an applicator around the globe of the eye, the applicator having at least one guide channel, and sliding a catheter into the guide channel of the applicator to thereby slide the catheter around the globe of the eye, the catheter containing a switchable x-ray source in a distal end of the catheter, to a position adjacent to the tumor, and switching on the x-ray source to emit radiation to deliver a prescription dose to the tumor.

46. The method of claim 45, wherein the applicator has a plurality of parallel guides, and including inserting the catheter into each of the parallel guides successively to deliver radiation in a desired distribution, avoiding concentration of radiation in ocular structure or adjacent tissue.

* * * * *